US011571344B2

(12) United States Patent
Onishi et al.

(10) Patent No.: US 11,571,344 B2
(45) Date of Patent: Feb. 7, 2023

(54) PANTS-TYPE DISPOSABLE DIAPER

(71) Applicant: LIVEDO CORPORATION, Ehime (JP)

(72) Inventors: Ryosuke Onishi, Tokushima (JP); Masaru Fujioka, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 666 days.

(21) Appl. No.: 16/497,459

(22) PCT Filed: Mar. 23, 2018

(86) PCT No.: PCT/JP2018/011621
§ 371 (c)(1),
(2) Date: Sep. 25, 2019

(87) PCT Pub. No.: WO2018/180958
PCT Pub. Date: Oct. 4, 2018

(65) Prior Publication Data
US 2020/0107971 A1    Apr. 9, 2020

(30) Foreign Application Priority Data
Mar. 28, 2017  (JP) .............................. JP2017-063861

(51) Int. Cl.
*A61F 13/49*      (2006.01)
*A61F 13/496*     (2006.01)
(Continued)

(52) U.S. Cl.
CPC ...... *A61F 13/496* (2013.01); *A61F 13/49009* (2013.01); *A61F 13/515* (2013.01);
(Continued)

(58) Field of Classification Search
CPC .......... A61F 13/49009; A61F 13/49011; A61F 13/49012; A61F 13/496; A61F 13/51404;
(Continued)

(56) References Cited

U.S. PATENT DOCUMENTS 8,986,276 B2 * 3/2015 Kawakami ............ A61F 13/496
                                                      604/385.24
9,913,764 B2 * 3/2018 Thomas ............ A61F 13/15593
(Continued)

FOREIGN PATENT DOCUMENTS

JP      2003-70838      3/2003
JP      2003-135515     5/2003
(Continued)

OTHER PUBLICATIONS

International Search Report dated May 15, 2018 in International (PCT) Application No. PCT/JP2018/011621.
(Continued)

*Primary Examiner* — Catharine L Anderson
(74) *Attorney, Agent, or Firm* — Wenderoth, Lind & Ponack, L.L.P.

(57) ABSTRACT

A pants-type disposable diaper (1) having a front body part (P), a back body part (Q) and a crotch part (R) positioned therebetween and formed in a pants shape, comprising an absorbent body (7) situated at least at the crotch part (R) and comprising a top sheet, a back sheet and an absorbent core (10) disposed therebetween, and an exterior member (2) provided on an outer side of the absorbent body (7) and situated at least at the front body part (P) and the back body part (Q), wherein the exterior member (2) comprises an outer sheet (5) and an inner sheet (6) provided on a skin-facing side of the outer sheet (5), and the outer sheet (5) is
(Continued)

made of a nonwoven fabric having a meltblown nonwoven layer and a printed part is provided to the skin-facing side of the outer sheet (5).

7 Claims, 4 Drawing Sheets

(51) Int. Cl.
    *A61F 13/514*     (2006.01)
    *A61F 13/511*     (2006.01)
    *A61F 13/515*     (2006.01)
    *A61F 13/15*     (2006.01)
    *A61F 13/84*     (2006.01)
    *A61L 15/26*     (2006.01)

(52) U.S. Cl.
    CPC .. *A61F 13/51121* (2013.01); *A61F 13/51401* (2013.01); *A61F 2013/1591* (2013.01); *A61F 2013/15967* (2013.01); *A61F 2013/8497* (2013.01); *A61L 15/26* (2013.01)

(58) Field of Classification Search
    CPC ...... A61F 13/51496; A61F 2013/49023; A61F 2013/49025; A61F 2013/8497
    See application file for complete search history.

(56) References Cited

U.S. PATENT DOCUMENTS

2001/0031954 A1* 10/2001 Jordan .............. A61F 13/51496
                                        604/385.01
2017/0156945 A1     6/2017 Hashimoto et al.

FOREIGN PATENT DOCUMENTS

| | | |
|---|---|---|
| JP | 2004-215694 | 8/2004 |
| JP | 2009-268525 | 11/2009 |
| JP | 2013-121428 | 6/2013 |
| JP | 2016-10517 | 1/2016 |
| JP | 2016-59650 | 4/2016 |

OTHER PUBLICATIONS

Notice of Reasons for Rejection dated May 19, 2020 in corresponding Japanese Patent Application No. JP2017-063861, with English translation.

* cited by examiner

[Fig. 1]
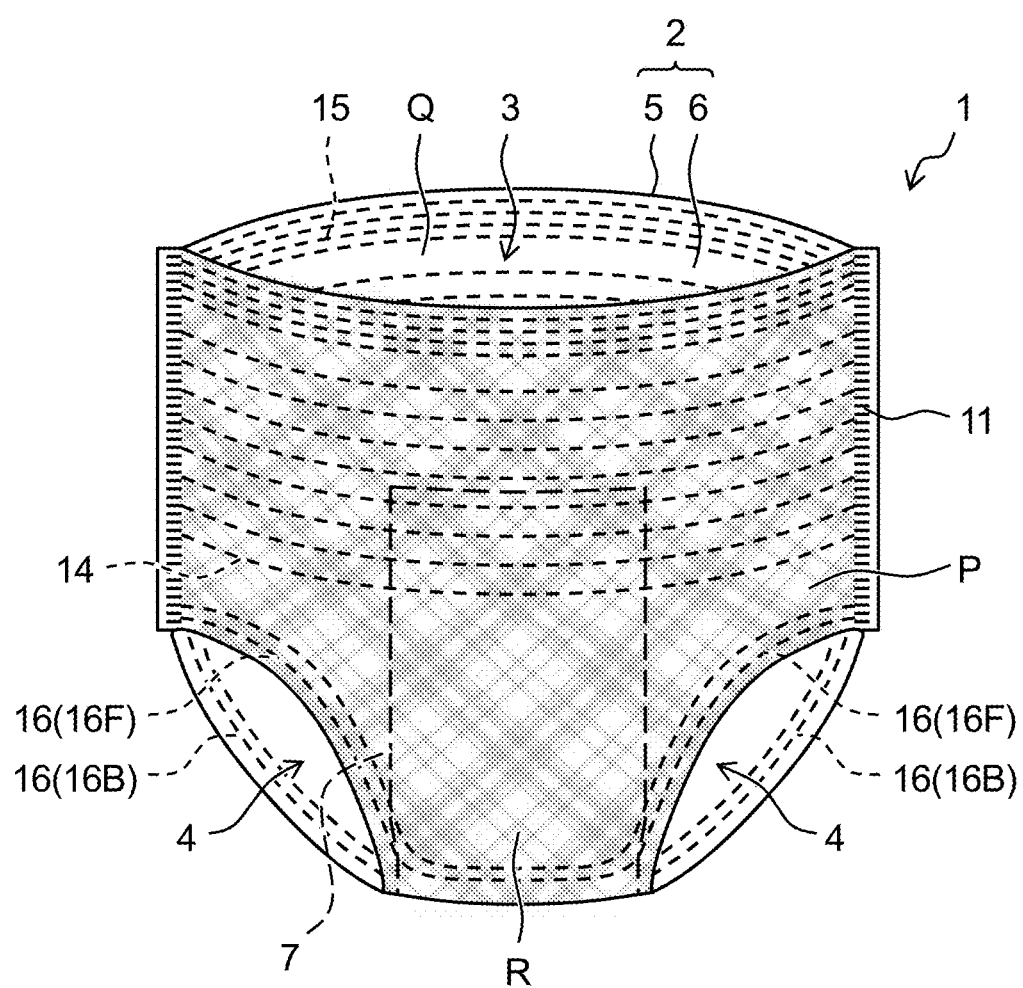

[Fig. 2]
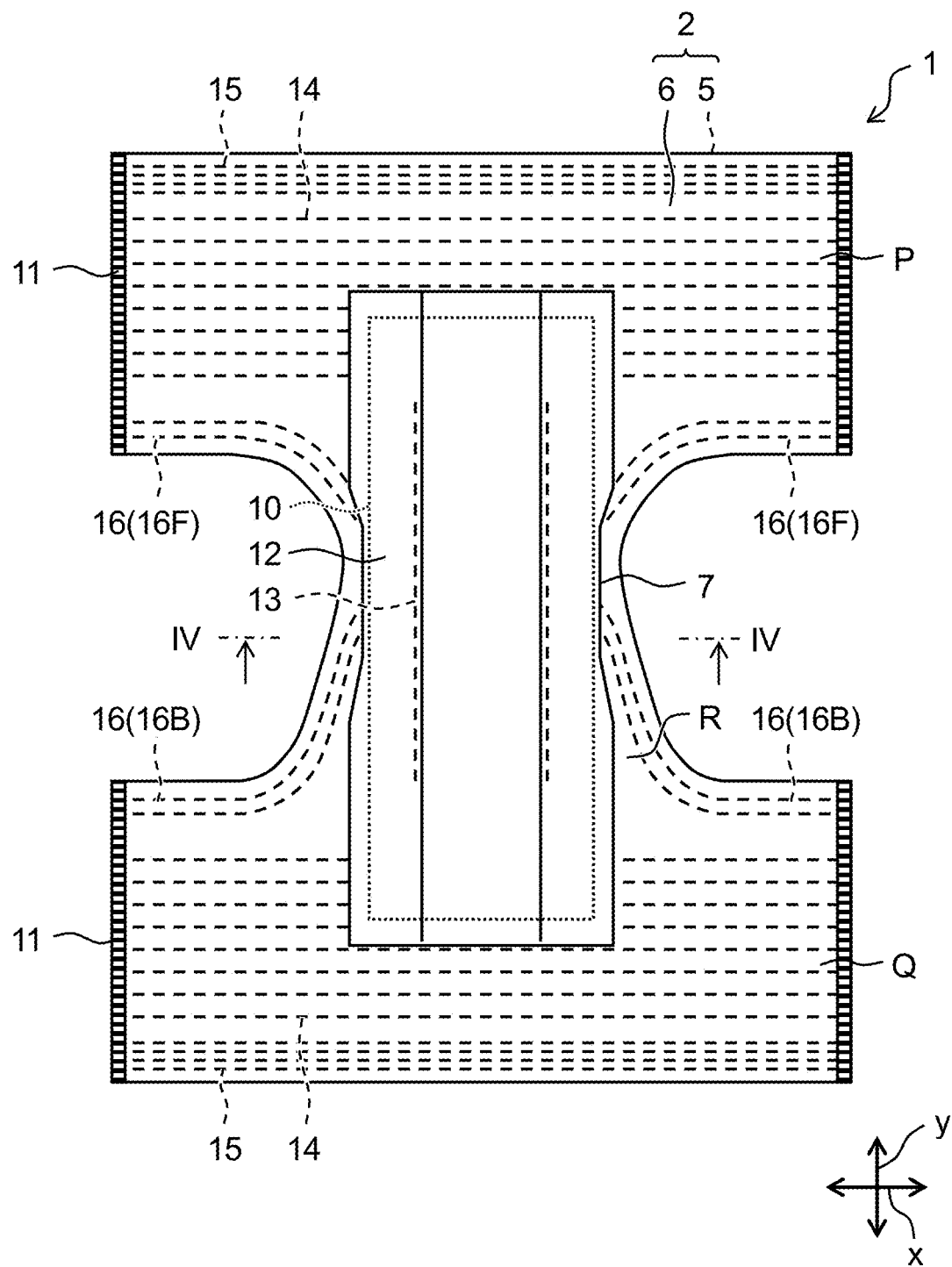

[Fig. 3]
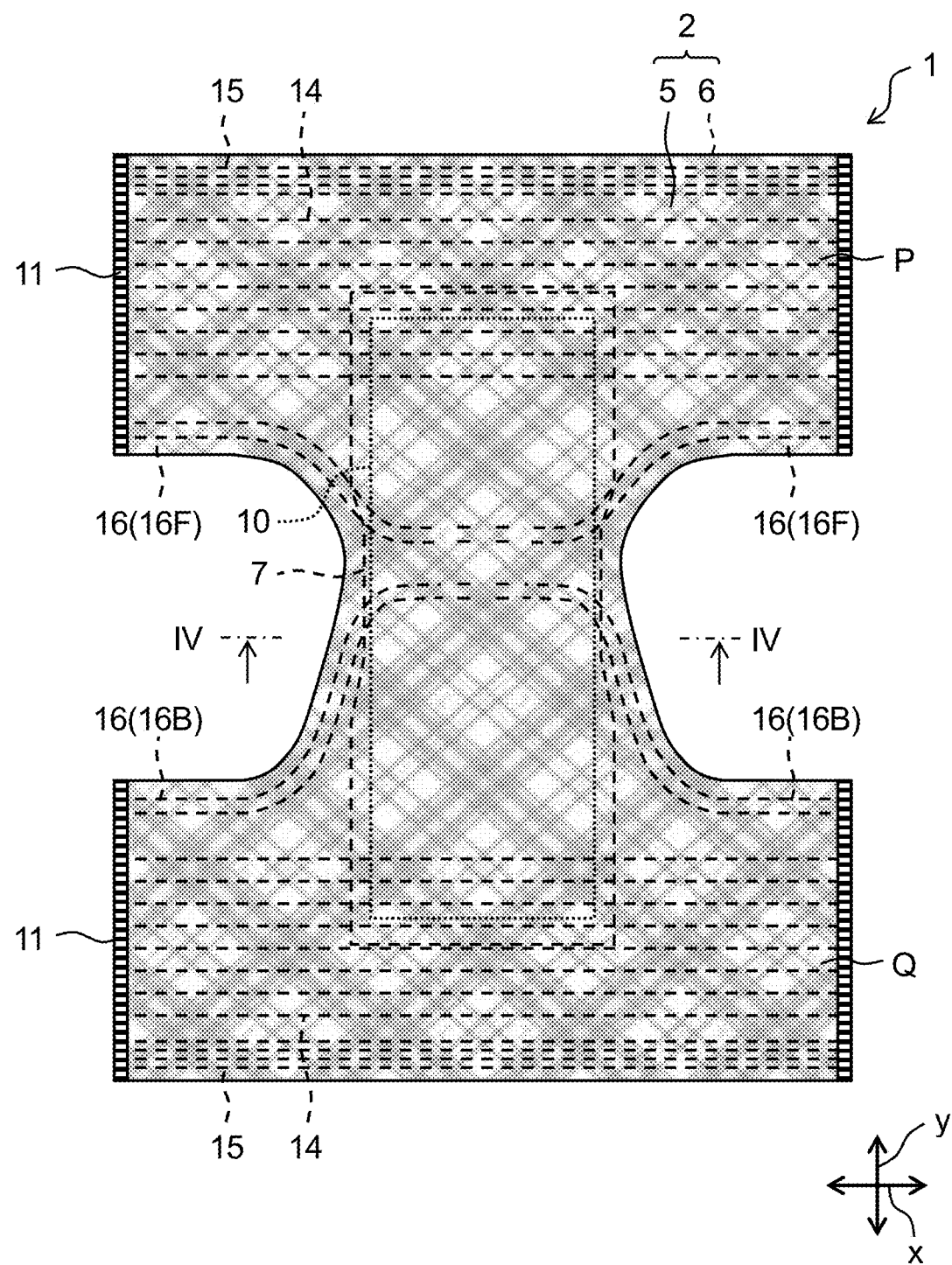

[Fig. 4]
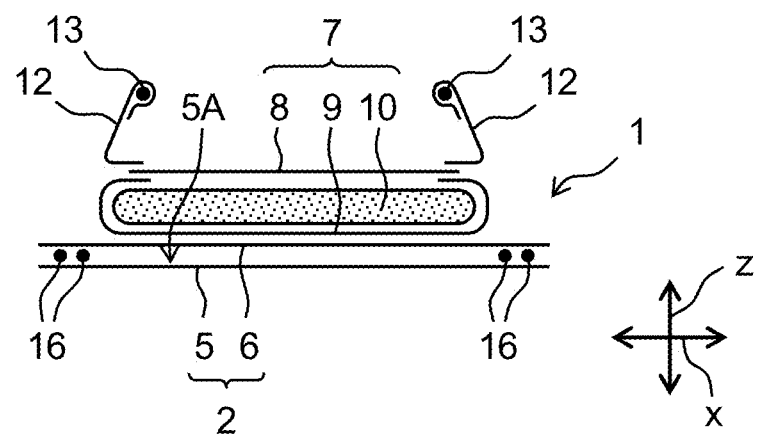

PANTS-TYPE DISPOSABLE DIAPER

TECHNICAL FIELD

The present invention relates to a pants-type disposable diaper.

BACKGROUND ART

Conventionally, a pants-type disposable diaper formed in the pants shape having a waist opening and a pair of leg openings is widely known. The pants-type disposable diaper is configured such that, for example, an exterior member is provided on an outer side of an absorbent body comprising a top sheet, a back sheet and an absorbent core disposed therebetween, and the exterior member is formed so as to include a front body part and a back body part or further include a crotch part. Among such pants-type disposable diapers, those provided with design or the like which is visible from the outside of the diaper are known. For example, Patent Literature 1 discloses a pants-type disposable diaper in which the exterior member comprises an outer sheet and an inner sheet and design is applied on the outer side of the inner sheet. Patent Literature 2 discloses a pants-type disposable diaper in which the exterior member comprises an outer sheet, an inner sheet and an intermediate sheet disposed therebetween and the intermediate sheet is provided with a decorative element which is visible from the outer side of the exterior member. In such diapers, designability can be enhanced by the design or the decoration element, and therefore, psychological resistance of a diaper user can be reduced.

CITATION LIST

Patent Literature

Patent Literature 1
  Japanese Unexamined Laid-open Patent Application Publication No. 2016-59650
Patent Literature 2
  Japanese Unexamined Laid-open Patent Application Publication No. 2016-10517

SUMMARY OF INVENTION

Technical Problem

As described above, pants-type disposable diapers provided with design or the like visible from the outside of the diaper are conventionally known, and in view of enhancing designability of the diaper, it is desirable that more elaborate design can be given to the diaper. The present invention has been achieved in view of the above circumstances, and the object of the present invention is to provide a pants-type disposable diaper which can provide high designability.

Solution to Problem

A pants-type disposable diaper of the present invention which solves the above problems is a diaper having a front body part, a back body part and a crotch part positioned therebetween and formed in a pants shape, comprising an absorbent body situated at least at the crotch part and comprising a top sheet, a back sheet and an absorbent core disposed therebetween, and an exterior member provided on an outer side of the absorbent body and situated at least at the front body part and the back body part, wherein the exterior member comprises an outer sheet and an inner sheet provided on a skin-facing side of the outer sheet, and the outer sheet is made of a nonwoven fabric having a meltblown nonwoven layer and a printed part is provided to the skin-facing side of the outer sheet.

In the pants-type disposable diaper of the present invention, since the outer sheet of the exterior member is made of a nonwoven fabric having a meltblown nonwoven layer and a printed part is provided to the skin-facing side of the outer sheet, the printed part can be visually recognized clearly, seen from the outer side of the diaper, whereby designability of the diaper can be enhanced. That is, a meltblown nonwoven layer is formed of a fine fiber layer and is like a film, and therefore, by making print to the skin-facing side of the outer sheet, the printed part is formed on the skin-facing side of the meltblown nonwoven layer, and design or the like formed by the print can be visually recognized clearly, seen from the outer side of the outer sheet. Hence, it becomes possible to give precise design to the exterior member, thereby improving designability of the diaper. In addition, by providing the printed part to the skin-facing side of the outer sheet, the printed part comes to be less likely to be lost during the production or use of the diaper, and the design applied to the diaper is likely to be maintained well.

It is preferable that the outer sheet is made of a laminated nonwoven fabric having a meltblown nonwoven layer and a spunbonded nonwoven layer provided on the outer side of the meltblown nonwoven layer. As the outer sheet is made of such nonwoven fabric, the printed design exhibits a gentle texture and the appearance can be made friendly for a user when seeing the printed part applied to the skin-facing side of the outer sheet from the outer side of the exterior member.

It is preferable that the inner sheet is made of a spunbonded nonwoven fabric. When the inner sheet is made of a spunbonded nonwoven fabric, the printed design applied to the skin-facing side of the outer sheet can be made inconspicuous, seen from the outer surface of the exterior member, and flexibility of the inner sheet is easily ensured.

It is preferable that the meltblown nonwoven layer is formed from fibers containing 10% by mass to 50% by mass of an α-olefin copolymer. When the meltblown nonwoven layer is constituted in this manner, it becomes easy to enhance flexibility of the meltblown nonwoven layer, resulting in easily ensuring flexibility of the outer sheet.

It is preferable that the nonwoven fabric constituting the outer sheet has an embossed surface on the skin-facing side and a non-embossed surface on the outer side. When the outer sheet is constituted in this manner, flexibility of the outer sheet can be enhanced. In addition, since the embosses of the skin-facing side of the outer sheet is made inconspicuous, seen from the outer side of the exterior member, the printed design applied to the skin-facing side of the outer sheet can be made conspicuous, compared with the case where the outer side of the outer sheet is an embossed surface.

It is preferable that a body elastic member extending in a width direction of the diaper is disposed between the outer sheet and the inner sheet at the front body part and the back body part of the exterior member, and the printed part is provided at least at the front body part and/or the back body part of the outer sheet. By providing the body elastic member, fittability around the trunk of the diaper can be enhanced; and in the pants-type disposable diaper of the present invention, even when the body elastic member is provided in this manner, the design or the like formed by the printed part can be visually recognized clearly, seen from the outer side of the exterior member, since the printed part is provided to the skin-facing side of the outer sheet.

It is preferable that the outer sheet and the inner sheet are bonded to each other via the body elastic member, and a non-bonded area of the outer sheet and the inner sheet is present so as to extend in the width direction of the diaper in the exterior member. By providing the non-bonded area extending in the width direction of the diaper, the printed design applied to the skin-facing side of the outer sheet becomes inconspicuous, seen from the skin-facing side of the exterior member, and flexibility of the exterior member can be enhanced.

Advantageous Effects of Invention

In the pants-type disposable diaper of the present invention, since the outer sheet of the exterior member is made of a nonwoven fabric having a meltblown nonwoven layer and the printed part is provided to the skin-facing side of the outer sheet, design or the like formed by the printed part can be visually recognized clearly, seen from the outer side of the outer sheet. Therefore, it becomes possible to give precise design to the exterior member and designability of the diaper can be enhanced.

BRIEF DESCRIPTION OF THE DRAWINGS

FIG. 1 shows a perspective view of a pants-type disposable diaper.

FIG. 2 shows a plan view of the pants-type disposable diaper shown in FIG. 1, seen from a skin-facing side, in a developed state where a front body part and a back body part are disjoined.

FIG. 3 shows a plan view of the pants-type disposable diaper shown in FIG. 1, seen from an outer side, in a developed state where a front body part and a back body part are disjoined.

FIG. 4 shows a cross-sectional view along a line VI-VI of the pants-type diaper shown in FIGS. 2 and 3.

DESCRIPTION OF THE PREFERRED EMBODIMENTS

A pants-type disposable diaper of the present invention has a front body part, a back body part and a crotch part positioned therebetween, and is formed in a pants shape having a waist opening and a pair of leg openings. The waist opening is an opening through which a wearer's trunk is put, and the leg opening is an opening through which a wearer's leg is put. The front body part means a part applied to an abdomen side of a wearer in wearing the diaper, and the back body part means a part applied to a back side of a wearer in wearing the diaper. In the pants-type disposable diaper, the front body part and the back body part correspond to parts located between the waist opening and the leg openings. The crotch part is positioned between the front body part and the back body part, and corresponds to a part applied to a crotch of a wearer. The crotch part is located between the pair of leg openings and is not joined to each other on both sides thereof in the width direction.

The pants-type disposable diaper has a front-back direction and a width direction. The front-back direction corresponds to a direction extending in a front-back direction in a crotch of the wearer when wearing the diaper. The width direction means a direction on the same plane as the pants-type disposable diaper and orthogonal to the front-back direction, and corresponds to a left-right direction of the wearer when wearing the diaper. The pants-type disposable diaper also has a skin-facing side and an outer side. The skin-facing side means a side facing a wearer's skin when wearing the diaper, and the outer side means a side facing away from the wearer when wearing the diaper.

The pants-type disposable diaper is configured that an exterior member is provided on an outer side of an absorbent body. The exterior member is provided so as to be visible from the outside of the diaper. The exterior member is preferably provided on the outermost side of the diaper. The absorbent body is preferably provided on the most skin-facing side of the diaper.

The absorbent body comprises a top sheet, a back sheet and an absorbent core disposed therebetween. The top sheet is provided on the skin-facing side of the absorbent core, and the back sheet is provided on the outer side of the absorbent core. The absorbent body is situated at least at the crotch part of the diaper and may further extend to the front body part and/or the back body part.

The exterior member is situated at least at the front body part and the back body part of the diaper, and may be further situated at the crotch part. For example, in the case where the exterior member is situated only at the front body part and the back body part, the absorbent body is provided so as to connect to the exterior member of the front body part and the exterior member of the back body part, and the absorbent body is provided so as to extend from the crotch part to the front body part and the back body part. In this case, a part of the absorbent body may be provided to be exposed to the outside of the diaper at the crotch part. Alternatively, the exterior member may be configured to include the front body part, the back body part and the crotch part positioned therebetween. In this case, the exterior member can be formed into a pants shape by joining the front body part and the back body part to each other on both lateral sides in the width direction.

The exterior member is basically provided so as to extend outward beyond the absorbent body in the width direction. Preferably, the exterior member is provided so as to extend outward beyond the absorbent body also in the front-back direction.

The top sheet is preferably liquid-permeable, and for example, a nonwoven fabric formed from hydrophilic fibers such as cellulose, rayon and cotton, a nonwoven fabric which is formed from hydrophobic fibers such as polyolefin (e.g., polypropylene, polyethylene), polyester (e.g., PET) and polyamide (e.g., nylon), and whose surface is hydrophilized with a surfactant, or the like can be used. As the top sheet, a woven fabric, a knitted fabric, a plastic film having holes may be also used.

The back sheet is preferably liquid-impermeable, and for example, a nonwoven fabric formed from hydrophobic fibers such as polyolefin (e.g., polypropylene, polyethylene), polyester (e.g., PET) and polyamide (e.g., nylon), a plastic film, or the like can be used. As the back sheet, a laminate of a nonwoven fabric and a plastic film may be also used.

In the case where the top sheet or the back sheet is made of a nonwoven fabric, a spunbonded nonwoven fabric, an air-through nonwoven fabric, a point-bonded nonwoven fabric, a meltblown nonwoven fabric, an airlaid nonwoven fabric, an SMS nonwoven fabric or the like is preferably used as the nonwoven fabric.

The absorbent core is not particularly restricted as long as it contains an absorbent material which is able to absorb excrement such as urine. As the absorbent core, a shaped product of an absorbent material, which is formed into a predefined shape, may be used. The absorbent core may be wrapped with a cover sheet such as a paper (e.g., a tissue paper and a thin paper) and a liquid-permeable nonwoven fabric. Examples of the absorbent material contained in the absorbent core include, for example, a hydrophilic fiber such as a cellulose fiber (e.g., a crushed pulp fiber), and an absorbent polymer such as a polyacrylic absorbent polymer, a polyasparaginic absorbent polymer, a cellulosic absorbent polymer, and a stark-acrylonitrile absorbent polymer. The absorbent material may include a thermal fusion fiber such as a polyolefin (e.g., polyethylene and polypropylene) fiber, a polyester (e.g., PET) fiber and a polyamide (e.g., nylon) fiber. These thermal fusion fibers may be hydrophilized with a surfactant or the like to increase affinity with bodily fluid such as urine.

The absorbent material preferably includes a hydrophilic fiber in view of increasing absorption rate of urine and the like. In addition, in view of enhancing absorption capacity, the absorbent material preferably includes an absorbent polymer. Therefore, the absorbent core preferably contains both a hydrophilic fiber (especially a pulp fiber) and an absorbent polymer. In this case, the absorbent material is preferably formed by mixing an absorbent polymer with a hydrophilic fiber assembly, or dispersing an absorbent polymer on a hydrophilic fiber assembly, for example.

The absorbent core may be a sheet-shaped absorbent body. Examples of the sheet-shaped absorbent body include an object which is formed to contain an absorbent polymer but not contain a pulp fiber between nonwoven fabrics. The sheet-shaped absorbent body formed in this manner enables high absorption capacity since it contains an absorbent polymer between nonwoven fabrics. In addition, since the sheet-shaped absorbent body does not contain a pulp fiber between nonwoven fabrics, it can be formed thin without being bulky.

For the sheet-shaped absorbent body, an absorbent fiber may be used as the absorbent material. Also in this case, the sheet-shaped absorbent body is formed thin without being bulky. Examples of the absorbent fiber include a fiber having a protonated carboxyl group or a carboxylate group. The absorbent fiber can be obtained by, for example, hydrolyzing an acrylic fiber, thereby converting a nitrile group contained in the acrylic fiber to a carboxylic group. The carboxyl group contained in the absorbent fiber preferably forms an alkaline metal salt or an ammonium salt. The absorbent fiber also can be prepared by immersing a hydrophilic fiber in acrylic acid to deposit acrylic acid on the surface of the fiber.

In the pants-type disposable diaper, rising flaps are preferably provided along both side edges in the width direction of the absorbent body. The rising flaps may be, for example, attached onto the top sheet of the absorbent body or may be provided at an outer position of the absorbent body in the width direction. The rising flap is preferably made of a liquid-impermeable or water-repellent nonwoven fabric, a plastic film or the like, and more preferably made of a water-repellent nonwoven fabric. By providing the rising flaps, lateral leakage of urine and the like can be prevented.

The rising flap is preferably provided with an elastic member for rising the flap in the vicinity of an upper end (that is, an end part on a wearer's side) thereof in the state of the rising flap standing. By the contraction force of the elastic member for rising the flap, rising gathers which stands toward a wearer is formed, and lateral leakage of urine and the like is prevented.

Details of the exterior member is explained below. The exterior member comprises an outer sheet and an inner sheet provided on the skin-facing side of the outer sheet. The outer sheet is disposed such that the outer surface thereof faces the outside of the diaper. The absorbent body is provided on the skin-facing side of the inner sheet. The outer sheet and the inner sheet may be liquid-permeable or liquid-impermeable, and sheet materials usable for the top sheet or the back sheet can be used.

The inner sheet and outer sheet are preferably made of a nonwoven fabric. As the nonwoven fabric, a spunbonded nonwoven fabric, an air-through nonwoven fabric, a point-bonded nonwoven fabric, a meltblown nonwoven fabric, an airlaid nonwoven fabric, an SMS nonwoven fabric or the like can be used; however, the outer sheet is made of a nonwoven fabric having at least a meltblown nonwoven layer. Examples of the nonwoven fabric having a meltblown nonwoven layer include a meltblown nonwoven fabric composed only of a meltblown nonwoven layer, an SM nonwoven fabric in which a spunbonded nonwoven layer is laminated on one side of a meltblown nonwoven layer, an SMS nonwoven fabric in which spunbonded nonwoven layers are laminated on both sides of a meltblown nonwoven layer, and others. The meltblown nonwoven layer means a nonwoven layer formed by a melt-blowing method, and the spunbonded nonwoven layer means a nonwoven layer formed by a spunbonding method. In the SM nonwoven fabric and the SMS nonwoven fabric, a plurality of meltblown nonwoven layers or a plurality of spunbonded nonwoven layers may be laminated; and for example, the SM nonwoven fabric includes an SMM nonwoven fabric, an SSM nonwoven fabric, an SSMM nonwoven fabric and the like, and the SMS nonwoven fabric includes an SMMS nonwoven fabric, an SSMS nonwoven fabric, an SSMSS nonwoven fabric, an SSMMS nonwoven fabric and the like.

As described above, the outer sheet of the exterior member is made of the nonwoven fabric having at least a meltblown nonwoven layer, and in addition thereto, printing is applied to the skin-facing side of the outer sheet. That is, in the exterior member, a printed part is provided to the skin-facing side of the outer sheet. Since the pants-type disposable diaper of the present invention is configured in this manner, the printed part applied to the exterior member is able to be visually recognized clearly, seen from the outside of the diaper, whereby designability of the diaper can be improved. Explaining about this, a meltblown nonwoven layer is formed of a fine fiber layer and is like a film, and therefore, by making print to the skin-facing side of the outer sheet, an ink remains on the surface of the skin-facing side of the meltblown nonwoven layer (that is, the ink does not penetrate the meltblown nonwoven layer so much) and a printed surface is formed on the skin-facing side of the meltblown nonwoven layer. Thus, the meltblown nonwoven layer is able to function like a celluloid sheet of an animation cel, and when seeing the outer sheet from the outer side, design or the like formed by the print can be visually recognized clearly. As a result, it becomes possible to give precise design to the exterior member, thereby improving designability of the diaper.

In the pants-type disposable diaper, the outer sheet may be made of a laminated nonwoven fabric in which a spunbonded nonwoven layer is laminated on the skin-facing side of the meltblown nonwoven layer. In this case, even if the print applied to the skin-facing side of the outer sheet is formed by directly printing to the spunbonded nonwoven layer, the ink can penetrate the spunbonded nonwoven layer to form a printed surface on the skin-facing side of the meltblown nonwoven layer, and therefore, design or the like formed by the print can be clearly seen from the outer side of the outer sheet. On the other hand, in the case where the outer sheet is made of, for example, a spunbonded nonwoven fabric which is composed only of a spunbonded nonwoven layer, when print is applied to the skin-facing side of the outer sheet, the ink penetrates the spunbonded nonwoven layer and tends to remain in the outer sheet unevenly in the thickness direction; and therefore, in this case, when seeing the outer sheet from the outer side, the outline of design or the like formed by the print tends to be blurred. Hence, it becomes difficult to give a fine printed design to the exterior member.

In the pants-type disposable diaper of the present invention, the effect of the printed part being less likely to be lost during the production or use of the diaper is also obtained by providing the printed part to the skin-facing side of the outer sheet. In the exterior member, since the skin-facing side of the outer sheet is a non-exposed surface to the outside, the printed part is less likely to rub off to be lost when the exterior member contacts a transport roller or the like during the production of the diaper or the exterior member contacts clothes or the like of a wearer during the use of the diaper.

The outer sheet is preferably provided with the printed part at least at the front body part and/or back body part, whereby designability of the diaper can be enhanced. More preferably, the outer sheet may be provided with the printed part at both the front body part and the back body part, and the printed part may also be provided at the crotch part. The printed part can be formed by using a conventionally known printing method such as gravure printing, flexographic printing, offset printing, inkjet printing, screen printing and the others.

The printed part to the skin-facing side of the outer sheet is preferably formed to be visible from the outer surface of the outer sheet, and at least a part of the printed part is preferably formed of a color other than white. More preferably, at least a part of the printed part to the skin-facing side of the outer sheet is formed of a chromatic color, whereby designability of the exterior member can be enhanced. Examples of the design formed by print include figures, illustrations, patterns, characters and the like.

The outer sheet is preferably made of a laminated nonwoven fabric having a meltblown nonwoven layer and a spunbonded nonwoven layer provided on the outer side of the meltblown nonwoven layer. Thus, the outer sheet is preferably made of an SM nonwoven (provided that the spunbonded nonwoven layer is located on the outer side of the outer sheet) or an SMS nonwoven. As the outer sheet is made of such nonwoven fabric, when the printed part applied to the skin-facing side of the outer sheet is seen from the outer side of the exterior member, the printed design exhibits a gentle texture and the appearance can be made more friendly for a user.

It is also preferable that the outer sheet is made of a laminated nonwoven fabric having a meltblown nonwoven layer and a spunbonded nonwoven layer provided on the skin-facing side of the meltblown nonwoven layer. Thus, the outer sheet is preferably made of an SM nonwoven (provided that the spunbonded nonwoven layer is located on the skin-facing side of the outer sheet) or an SMS nonwoven. As the outer sheet is made of such nonwoven fabric, the printed surface on the meltblown nonwoven layer is protected by the spunbonded nonwoven layer, and so, even in the case where an elastic member is disposed between the outer sheet and the inner sheet, the printed part on the skin-facing side of the outer sheet is less likely to be lost.

It is more preferable that the outer sheet is made of a laminated nonwoven fabric in which spunbonded nonwoven layers are provided on both sides (namely, the outer side and the skin-facing side) of a meltblown nonwoven layer. Thus, the outer sheet is preferably made of an SMS nonwoven fabric. When the outer sheet is made of such nonwoven fabric, designability of the diaper can be much improved and the printed part on the skin-facing side of the outer sheet can be made hard to be lost.

Mass per unit area of the meltblown nonwoven layer of the outer sheet is, for example, preferably 1 $g/m^2$ or more, more preferably 2 $g/m^2$ or more, and preferably 18 $g/m^2$ or less, more preferably 12 $g/m^2$ or less, even more preferably 8 $g/m^2$ or less. When the meltblown nonwoven layer of the outer sheet is formed in this manner, the printed surface is easily formed on the meltblown nonwoven layer, and the meltblown nonwoven layer does not become too thick, that facilitates securing flexibility of the outer sheet.

Mass per unit area of the spunbonded nonwoven layer of the outer sheet is, for example, preferably 3 $g/m^2$ or more, more preferably 4 $g/m^2$ or more, even more preferably 5 $g/m^2$ or more, and preferably 12 $g/m^2$ or less, more preferably 10 $g/m^2$ or less, even more preferably 8 $g/m^2$ or less. When the spunbonded nonwoven layer of the outer sheet is formed in this manner, the effect of providing the spunbonded nonwoven layer in the outer sheet is likely to be exerted suitably, and in the case where the spunbonded nonwoven layer is provided on the skin-facing side of the meltblown nonwoven layer, the printed surface is likely to be suitably formed on the meltblown nonwoven layer.

Mass per unit area of the outer sheet is, for example, preferably 8 $g/m^2$ or more, more preferably 12 $g/m^2$ or more, even more preferably 15 $g/m^2$ or more, and preferably 36 $g/m^2$ or less, more preferably 30 $g/m^2$ or less, even more preferably 24 $g/m^2$ or less. By forming the outer sheet in this manner, it becomes easy to form the outer sheet flexibly without making it rigid while securing the strength of the outer sheet.

The meltblown nonwoven layer of the outer sheet is preferably formed from fibers containing 10% by mass to 50% by mass of an $\alpha$-olefin copolymer. When the meltblown nonwoven layer of the outer sheet is constituted in this manner, it becomes easy to enhance flexibility of the meltblown nonwoven layer, resulting in easily ensuring flexibility of the outer sheet. The content of the $\alpha$-olefin copolymer in the constituent fibers of the meltblown nonwoven layer is more preferably 15% by mass or more, even more preferably 20% by mass or more, and more preferably 45% by mass or less, even more preferably 40% by mass or less.

The $\alpha$-olefin copolymer is not particularly limited as long as it is a copolymer of two or more kinds of $\alpha$-olefin, and a copolymer of $\alpha$-olefin having 2 to 10 carbon atoms is more preferable. The $\alpha$-olefin copolymer is preferably a random copolymer of $\alpha$-olefin. Examples of $\alpha$-olefin include, for example, ethylene, propylene, 1-butene, 1-pentene, 1-hexene, 4-methyl-1-pentene, 1-octene, 1-decene and others. The $\alpha$-olefin copolymer may have a monomer unit other than $\alpha$-olefin, and may have, for example, a unit derived from a diene compound. This diene compound is preferably a non-conjugated diene compound, and examples of that includes, for example, a chain non-conjugated diene such as 1,4-hexadiene, 1,6-octadiene and 2-methyl-1,5-hexadiene, a cyclic non-conjugated diene such as cyclohexadiene, and others. The $\alpha$-olefin copolymer preferably contains a unit derived from $\alpha$-olefin as a main component, and the content of the unit derived from $\alpha$-olefin in 100% by mass of the $\alpha$-olefin copolymer is preferably 50% by mass or more, more preferably 70% by mass or more, even more preferably 80% by mass or more, and further more preferably 90% by mass or more. The $\alpha$-olefin copolymer may contain only units derived from $\alpha$-olefin.

The α-olefin copolymer is preferably a copolymer of ethylene and α-olefin having 3 to 20 carbon atoms, or a copolymer of propylene and α-olefin having 4 to 20 carbon atoms. In the case that the α-olefin copolymer is a copolymer of ethylene and α-olefin having 3 to 20 carbon atoms, the content of a unit derived from ethylene in the α-olefin copolymer is preferably higher than the content of a unit derived from α-olefin having 3 to 20 carbon atoms on molar basis. In the case that the α-olefin copolymer is a copolymer of propylene and α-olefin having 4 to 20 carbon atoms, the content of a unit derived from propylene in the α-olefin copolymer is preferably higher than the content of a unit derived from an α-olefin having 4 to 20 carbon atoms on molar basis.

It is preferable that the nonwoven fabric constituting the outer sheet is an embossed nonwoven fabric. When the outer sheet is made of an embossed nonwoven fabric, flexibility of the outer sheet can be enhanced and the wearing feeling of the diaper can be improved. In view of making the printed design applied to the skin-facing side of the outer sheet conspicuous seen from the outer side of the exterior member, it is preferable that the outer sheet has an embossed surface on the skin-facing side and a non-embossed surface on the outer side. When the outer side of the outer sheet is a non-embossed surface, the embosses of the skin-facing side of the outer sheet is made inconspicuous seen from the outer side of the exterior member, and the printed design applied to the skin-facing side of the outer sheet can be made conspicuous, compared with the case where the outer side of the outer sheet is an embossed surface.

The nonwoven fabric constituting the outer sheet may be formed so that a total light transmittance is low to some extent. As described above, the pants-type disposable diaper of the present invention is configured such that the printed design applied to the skin-facing side of the outer sheet can be visually recognized clearly, seen from the outer side of the exterior member; and hence, the nonwoven fabric of the outer sheet can be formed so that the total light transmittance is low to some extent, whereby visually shielding effect by the outer sheet can be enhanced. The total light transmittance of the nonwoven fabric of the outer sheet may be, for example, 30% or higher, 40% or higher, or 50% or higher. The upper limit of the total light transmittance of the nonwoven fabric of the outer sheet is not particularly limited, and is preferably 85% or lower, more preferably 80% or lower, and even more preferably 75% or lower. The total light transmittance of the nonwoven fabric of the outer sheet described herein means a total light transmittance of the nonwoven fabric of the outer sheet before printing and means a total light transmittance of a non-printed part of the outer sheet. The total light transmittance is measured in accordance with JIS K 7375: 2008.

Meanwhile, the inner sheet is preferably made of a spunbonded nonwoven fabric or an air-through nonwoven fabric, and more preferably made of a spunbonded nonwoven fabric. When the inner sheet is made of such nonwoven fabric, the inner sheet is formed relatively bulky, and the printed design applied to the skin-facing side of the outer sheet can be made inconspicuous seen from the outer surface of the exterior member. In particular, by forming the inner sheet from a spunbonded nonwoven fabric, flexibility of the inner sheet can be easily secured. In the present invention, a spunbonded nonwoven fabric means a nonwoven fabric composed only of a spunbonded nonwoven layer.

Mass per unit area of the inner sheet is, for example, preferably 8 $g/m^2$ or more, more preferably 12 $g/m^2$ or more, even more preferably 15 $g/m^2$ or more, and preferably 36 $g/m^2$ or less, more preferably 30 $g/m^2$ or less, even more preferably 24 $g/m^2$ or less. By forming the inner sheet in this manner, it becomes easy to form the inner sheet flexibly without making it rigid while securing strength of the inner sheet.

The total light transmittance of the inner sheet is not particularly limited, and in view of making the printed design applied to the skin-facing side of the outer sheet inconspicuous seen from the skin-facing side of the exterior member, the total light transmittance of the nonwoven fabric of the inner sheet is preferably lower than that of the outer sheet. The total light transmittance of the inner sheet may be, for example, 10% or higher, 25% or higher, or 40% or higher. The upper limit of the total light transmittance of the inner sheet is not particularly limited, and is preferably 85% or lower, more preferably 80% or lower, and even more preferably 75% or lower. The total light transmittance of the inner sheet described herein means a total light transmittance of a sheet material constituting the inner sheet, and in the case where the inner sheet is made of a nonwoven fabric, it means a total light transmittance of the nonwoven fabric constituting the inner sheet.

It is preferable that the inner sheet is partially bonded to the outer sheet. That is, it is preferable that the outer sheet and the inner sheet are not bonded to each other at their entire surface, but are bonded to each other at a bonding part partially provided to the outer sheet and the inner sheet. By partially bonding the outer sheet and the inner sheet, the printed design applied to the skin-facing side of the outer sheet can be made inconspicuous seen from the skin-facing side of the exterior member. The shape and arrangement of the bonding part are not particularly limited in this case. The bonding part may be, for example, provided in a scattered pattern in any shape, or may be provided in a lattice pattern or a line pattern. In the case where the bonding parts are provided in a scattered pattern, the shape of each of the bonding parts is not particularly limited and may be circular, oval, polygonal, wavy, star-like or the like, and these may be provided in a regular arrangement pattern or a random arrangement pattern. In the case where the bonding parts are provided in a lattice pattern or a line pattern, each line constituting the lattice or line pattern may be a straight line, a wavy line, a zigzag line or the like, and in this case, each line is preferably provided over substantially the entire width direction or front-back direction of the outer sheet or the inner sheet.

In the exterior member, various elastic members can be provided between the outer sheet and the inner sheet. When an elastic member is provided to the exterior member, fittability of the pants-type disposable diaper can be improved and the effect of leakage prevention can be enhanced.

For example, it is preferable that a body elastic member extending in the width direction of the diaper is provided between the outer sheet and the inner sheet at the front body part and the back body part of the exterior member, and thereby, fittability around a wearer's trunk can be enhanced. In the pants-type disposable diaper of the present invention, even in the case where, for example, the printed part is provided at the front body part and/or the back body part of the exterior member and the body elastic member is provided at the front body part and the back body part, the design or the like formed by the printed part can be visually recognized clearly, seen from the outer side of the exterior member, since the printed part is provided to the skin-facing side of the outer sheet. Thus, even when the front body part or the back body part of the exterior member is shrunk in the width direction of the diaper due to the contraction force of the body elastic member, the printed design on the skin-facing side of the outer sheet can be visually recognized clearly without being blurred, seen from the outer side of the exterior member.

The body elastic member is preferably bonded to the outer sheet and the inner sheet. That is, it is preferable that the outer sheet and the inner sheet are bonded to each other via the body elastic member. In this case, it is preferable that in the exterior member, a non-bonded area of the outer sheet and the inner sheet is present so as to extend in the width direction of the diaper, whereby the printed design applied to the skin-facing side of the outer sheet becomes to be inconspicuous, seen from the skin-facing side of the exterior member. In addition, flexibility of the exterior member can be enhanced, compared with the case where the outer sheet and the inner sheet are entirely bonded. The body elastic member is preferably bonded to the outer sheet and the inner sheet in a stretched state.

It is preferable that a plurality of the body elastic members are provided so as to be arranged in the front-back direction at the front body part and/or the back body part. In addition, among the body elastic members, elastic members arranged at narrow intervals in the front-back direction along the edge of the waist opening may be provided as waist elastic members; and thereby, waist gathers around the waist of a wearer is formed and leakage of excrement such as urine from the back side or the abdomen side is prevented.

In view of enhancing flexibility of the exterior member, it is also preferred that the body elastic member is bonded to the outer sheet and the inner sheet only at both end parts thereof (for example, only a part within 30 mm from the end of the body elastic member) and a middle part positioned between the both end parts is not bonded to the outer sheet and the inner sheet. In this case, it is preferable that the outer sheet and the inner sheet are bonded to each other at bonding parts aligned in the width direction of the diaper between the plurality of body elastic members arranged in the front-back direction; and thereby, arrangement position of the body elastic member can be limited in a certain range and flexibility of the exterior member can be secured.

It is preferable that the outer sheet is folded back toward the inner sheet at the edge of the waist opening. Thereby, the edge of the waist opening of the exterior member can be formed neat. In this case, at least a part of the body elastic members may be disposed between the outer sheets folded back at the edge of the waist opening.

In the exterior member, a leg elastic member may be disposed along the edge of the leg opening, thereby preventing leakage of excrement such as urine from the leg opening. The number of elastic members constituting the leg elastic member is not particularly limited, and a plurality of elastic members are preferably provided side by side. The leg elastic member is preferably peovided between the outer sheet and the inner sheet.

As each elastic member provided in the pants-type disposable diaper, elastic materials such as a polyurethane thread, a polyurethane film, a natural rubber and the like, that are generally used for disposable diapers, can be used. Each elastic member is preferably attached in a stretched state using a known bonding means such as an adhesive (e.g., a hot-melt adhesive) or welding (e.g., ultrasonic welding). For example, a polyurethane thread having a fineness of 40 dtex to 1,240 dtex is stretched at a ratio of 1.1 to 5.0 times and disposed to be fixed. As the adhesive, a rubber hot-melt adhesive is preferably used. Regarding the above-described ratio, an unexpanded state is defined as 1.0 time.

Next, a pants-type disposable diaper of the present invention is explained with reference to the drawings. However, the present invention is not limited to the embodiment shown in the drawings. FIGS. 1 to 4 show an example of a pants-type disposable diaper of the present invention. FIG. 1 shows a perspective view of a pants-type disposable diaper, FIG. 2 shows a plan view of the pants-type disposable diaper shown in FIG. 1 seen from a skin-facing side in a developed state where a front body part and a back body part are disjoined, FIG. 3 shows a plan view of the pants-type disposable diaper shown in FIG. 1 seen from an outer side in a developed state where a front body part and a back body part are disjoined, and FIG. 4 shows a cross-sectional view along a line VI-VI of the pants-type disposable diaper shown in FIGS. 2 and 3. In the drawings, an arrow x represents a width direction of the diaper, an arrow y represents a front-back direction of the diaper, and an arrow z represents a thickness direction of the diaper.

A pants-type disposable diaper 1 has a front body part P, a back body part Q and a crotch part R positioned therebetween, and is formed in a pants shape having a waist opening 3 and a pair of leg openings 4. In the pants-type disposable diaper 1, an absorbent body 7 is provided at least at the crotch part R, and an exterior member 2 is provided on an outer side of the absorbent body 7. The exterior member 2 only needs to be situated at least at the front body part P and the back body part Q, and in the drawings, the exterior member 2 is also situated at the crotch part R. Thus, the exterior member 2 has the front body part P, the back body part Q and the crotch part R positioned therebetween, and is formed into a pants shape by joining the front body part P and the back body part Q at side joining parts 11 on both sides in the width direction x. The front body part P and the back body part Q correspond to parts located between the waist opening 3 and the leg opening 4 in the front-back direction y.

The absorbent body 7 comprises a top sheet 8, a back sheet 9 and an absorbent core 10 disposed therebetween (see FIGS. 2 and 4). The absorbent body 7 only needs to be present at least at the crotch part R of the pants-type disposable diaper 1 and preferably extends to the front body part P and/or the back body part Q. The absorbent body 7 and the absorbent core 10 are formed in, for example, a substantially hourglass shape or a substantially rectangular shape.

It is preferable that the absorbent body 7 is provided with rising flaps 12 on both sides thereof in the width direction x. The rising flap 12 enables preventing leakage of excrement such as urine and the like. The rising flap 12 is preferably provided with a rising elastic member 13 at an upper end part thereof in its standing state (an end part of a wearer's side). The rising flap 12 is promoted to stand by contractive force of the rising elastic member 13.

The exterior member 2 comprises an outer sheet 5 and an inner sheet 6 provided on the skin-facing side of the outer sheet 5. The outer sheet 5 is made of a nonwoven fabric having a meltblown nonwoven layer, and a printed part is provided to the skin-facing side 5A of the outer sheet 5 (see, FIG. 4). As the exterior member is configured in this manner, the printed design applied to the skin-facing side 5A of the outer sheet 5 can be visually recognized clearly, seen from the outer side of the exterior member 2, whereby designability of the diaper can be enhanced. The outer sheet 5 is preferably made of a laminated nonwoven fabric having a meltblown nonwoven layer and a spunbonded nonwoven layer provided on the outer side of the meltblown nonwoven layer, and is more preferably made of an SMS nonwoven fabric in which spunbonded nonwoven layers are provided on both sides of a meltblown nonwoven layer. Meanwhile, the inner sheet 6 is preferably made of a spunbonded nonwoven fabric, whereby the printed design applied to the skin-facing side 5A of the outer sheet 5 is made inconspicuous, seen from the skin-facing side of the exterior member 2, and flexibility of the inner sheet 6 is easily secured.

As shown in FIGS. 1 to 3, it is preferable that a body elastic member 14 extending in the width direction x is disposed between the outer sheet 5 and the inner sheet 6 at the front body part P and the back body part Q of the exterior member 2. By disposing the body elastic member 14, fittability around a wearer's trunk can be enhanced. On the skin-facing side 5A of the outer sheet 5, the printed part is preferably provided at least at the front body part P and/or the back body part Q. In the pants-type disposable diaper 1, even when the body elastic members 14 is provided at the front body part P and the back body part Q of the exterior member 2 and the exterior member 2 is contracted in the width direction x, the printed design applied to the skin-facing side 5A of the outer sheet 5 can be visually recognized clearly. It is preferable that the outer sheet 5 and the inner sheet 6 are bonded to each other via the body elastic member 14 and a non-bonded area of the outer sheet 5 and the inner sheet 6 is present so as to extend in the width direction x in the exterior member 2. When the non-bonded part is formed in this manner between the outer sheet 5 and the inner sheet 6, the print design applied to the skin-facing side 5A of the outer sheet 5 becomes inconspicuous, seen from the skin-facing side of the exterior member 2, and flexibility of the exterior member 2 can be enhanced.

Among the body elastic members 14, elastic members disposed along the edge of the waist opening 3 at narrow intervals in the front-back direction y may be referred to as waist elastic members 15. Thereby, waist-gathers around a wearer's waist is formed, and leakage of excrement such as urine from a back side or an abdomen side of the diaper is prevented.

It is preferable that a leg elastic member 16 is provided to the exterior member 2 along an edge of the leg opening 4. The leg elastic member 16 is preferably disposed between the outer sheet 5 and the inner sheet 6. In the drawings, the leg elastic member 16 consists of a front leg elastic member 16F disposed along a front side of the edge of the leg opening 4 and a back leg elastic member 16B disposed along a back side of the edge of the leg opening 4. The front leg elastic member 16F and the back leg elastic member 16B gives elastic members disposed along almost the entire circumference of the edge of the leg opening 4. The leg elastic member 16 forms leg-gathers around the wearer's leg, whereby leakage of excrement such as urine from the crotch is prevented. In the drawings, the front leg elastic member 16F and the back leg elastic member 16B are disposed separately from each other, however, the front leg elastic member 16F and the back leg elastic member 16B may be disposed in contact with each other or disposed so as to intersect with each other.

It is preferable that the leg elastic member 16 is disposed intermittently at a part crossing the crotch part R in the width direction x. Thereby, distortion of the absorbent body 7 or the absorbent core 10 can be reduced in the crotch part R. As a method of intermittently disposing the leg elastic members 16, for example, the leg elastic member 16 may be attached to the exterior member 2, followed by cutting the leg elastic members 16 by a cutter or the like. At this time, the leg elastic member 16 is preferably cut at a plurality of places.

This application claims priority to Japanese Patent Application No. 2017-063861, filed on Mar. 28, 2017, the entire contents of which are incorporated by reference herein.

REFERENCE SIGNS LIST

1: a pants-type disposable diaper
2: an exterior member
3: a waist opening
4: a leg opening
5: an outer sheet
6: an inner sheet
7: an absorbent body
8: a top sheet
9: a back sheet
10: an absorbent core
14: a body elastic member
15: a waist elastic member
16: a leg elastic member

The invention claimed is:

1. A pants-type disposable diaper comprising:
a front body part;
a back body part;
a crotch part positioned between the front body part and the back body part;
an absorbent body situated at least at the crotch part and comprising a top sheet, a back sheet and an absorbent core disposed, therebetween; and
an exterior member provided on an outer side of the absorbent body and situated at least at the front body part and the back body part, wherein
the exterior member comprises an outer sheet and an inner sheet provided on a skin-facing side of the outer sheet,
the outer sheet is made of a nonwoven fabric having a meltblown nonwoven layer and a printed part is provided to the skin-facing side of the outer sheet,
the nonwoven fabric constituting the outer sheet has an embossed surface on the skin-facing side and a non-embossed surface on the outer side, and
a total light transmittance of the nonwoven fabric constituting the outer sheet is 30% or higher and 75% or lower.

2. The pants-type disposable diaper according to claim 1, wherein the outer sheet is made of a laminated nonwoven fabric having a meltblown nonwoven layer and a spunbonded nonwoven layer provided on the outer side of the meltblown nonwoven layer.

3. The pants-type disposable diaper according to claim 2, wherein the inner sheet is made of a spunbonded nonwoven fabric.

4. The pants-type disposable diaper according to claim 1, wherein the meltblown nonwoven layer is formed from fibers containing 10% by mass to 50% by mass of an α-olefin copolymer.

5. The pants-type disposable diaper according to claim 1, wherein
a body elastic member extending in a width direction of the diaper is disposed between the outer sheet and the inner sheet at the front body part and the back body part of the exterior member, and
the printed part is provided at least at the front body part and/or the back body part of the outer sheet.

6. The pants-type disposable diaper according to claim 5, wherein
the outer sheet and the inner sheet are bonded to each other via the body elastic member, and a non-bonded area of the outer sheet and the inner sheet is present so as to extend in the width direction of the diaper in the exterior member.

7. The pants-type disposable diaper according to claim 1, wherein a total light transmittance of a nonwoven fabric constituting the inner sheet is lower than the total light transmittance of the nonwoven fabric constituting the outer sheet.

\* \* \* \* \*